(12) United States Patent
Calle et al.

(10) Patent No.: US 8,548,595 B1
(45) Date of Patent: Oct. 1, 2013

(54) METHODS AND SYSTEMS FOR MANAGING COCHLEAR IMPLANT FITTING SOFTWARE FEATURES

(75) Inventors: Guillermo A. Calle, Moorpark, CA (US); Fernando Chapa, Harold, CA (US); Carlos O. Hernandez, Stevenson Ranch, CA (US)

(73) Assignee: Advanced Bionics AG, Zug (CH)

( * ) Notice: Subject to any disclaimer, the term of this patent is extended or adjusted under 35 U.S.C. 154(b) by 369 days.

(21) Appl. No.: 12/847,205

(22) Filed: Jul. 30, 2010

(51) Int. Cl.
*A61N 1/08* (2006.01)
(52) U.S. Cl.
USPC ............... 607/57; 607/55; 607/56; 607/137
(58) Field of Classification Search
USPC ... 623/10; 607/9, 55–57, 137; 381/312–316, 381/328–330
See application file for complete search history.

(56) References Cited

U.S. PATENT DOCUMENTS

| | | | |
|---|---|---|---|
| 6,073,049 A * | 6/2000 | Alt et al. | 607/31 |
| 6,289,247 B1 * | 9/2001 | Faltys et al. | 607/57 |
| 8,047,207 B2 * | 11/2011 | Perez et al. | 128/864 |
| 2007/0100397 A1 * | 5/2007 | Seeberger et al. | 607/60 |

* cited by examiner

*Primary Examiner* — Joseph Stoklosa
(74) *Attorney, Agent, or Firm* — ALG Intellectual Property, LLC

(57) ABSTRACT

An exemplary method of managing cochlear implant fitting software includes a cochlear implant fitting subsystem maintaining data representative of a cochlear implant fitting software package comprising a plurality of cochlear implant fitting features, maintaining data representative of a plurality of independent licensing heuristics corresponding to the plurality of cochlear implant fitting features, and selectively enabling or disabling each cochlear implant fitting feature within the plurality of cochlear implant fitting features in accordance with the corresponding independent licensing heuristic. Corresponding methods and systems are also described.

13 Claims, 11 Drawing Sheets

METHODS AND SYSTEMS FOR MANAGING COCHLEAR IMPLANT FITTING SOFTWARE FEATURES

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When a cochlear implant system is initially implanted in a patient, and during follow-up tests and checkups thereafter, it is usually necessary to "fit" the cochlear implant system to the patient. Fitting of a cochlear implant system to a patient is typically performed by an audiologist or the like who presents various stimuli to the patient and relies on subjective feedback from the patient as to how such stimuli are perceived. Adjustments may be made to specifically tailor the parameters of the cochlear implant system to the patient being fitted.

Fitting a cochlear implant system to a patient typically utilizes and/or is performed by cochlear implant fitting hardware that implements and/or operates in accordance with cochlear implant fitting software. Like other medical-related products, cochlear implant fitting software is regulated by governmental agencies from geographic regions (e.g., countries, states, provinces, etc.) where the cochlear implant fitting software is released. Because the regulation of the fitting software may differ from one geographic region to the next, it may be necessary produce several different versions of the cochlear implant fitting software, with each different version corresponding to the specific regulations/limitations of a particular geographic region. However, the process of creating, testing, debugging, releasing, and managing multiple versions of cochlear implant fitting software can be burdensome and expensive. This problem is further exacerbated by the fact that each version of the cochlear implant fitting software must pass through a regulatory approval process.

SUMMARY

An exemplary method of managing cochlear implant fitting software includes a cochlear implant fitting subsystem 1) maintaining data representative of a cochlear implant fitting software package comprising a plurality of cochlear implant fitting features, 2) maintaining data representative of a plurality of independent licensing heuristics corresponding to the plurality of cochlear implant fitting features, and 3) selectively enabling or disabling each cochlear implant fitting feature in accordance with the corresponding independent licensing heuristic.

Another exemplary method of managing cochlear implant fitting software includes a cochlear implant fitting subsystem 1) maintaining data representative of a cochlear implant fitting software package comprising a plurality of cochlear implant fitting features, 2) maintaining data representative of a plurality of independent licensing heuristics corresponding to the plurality of cochlear implant fitting features, 3) detecting a satisfaction of one or more licensing conditions specified by a particular independent licensing heuristic corresponding to a particular cochlear implant fitting feature, 4) enabling the particular cochlear implant fitting feature in response to the detecting the satisfaction of the one or more licensing conditions, and 5) performing one or more cochlear implant fitting operations in accordance with the particular cochlear implant fitting feature.

An exemplary system for managing cochlear implant fitting software includes 1) a storage facility configured to maintain data representative of a cochlear implant fitting software package comprising a plurality of cochlear implant fitting features and maintain data representative of a plurality of independent licensing heuristics corresponding to the plurality of cochlear implant fitting features, and 2) a feature control facility communicatively coupled to the storage facility and configured to selectively enable or disable each cochlear implant fitting feature in accordance with the corresponding independent licensing heuristic.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
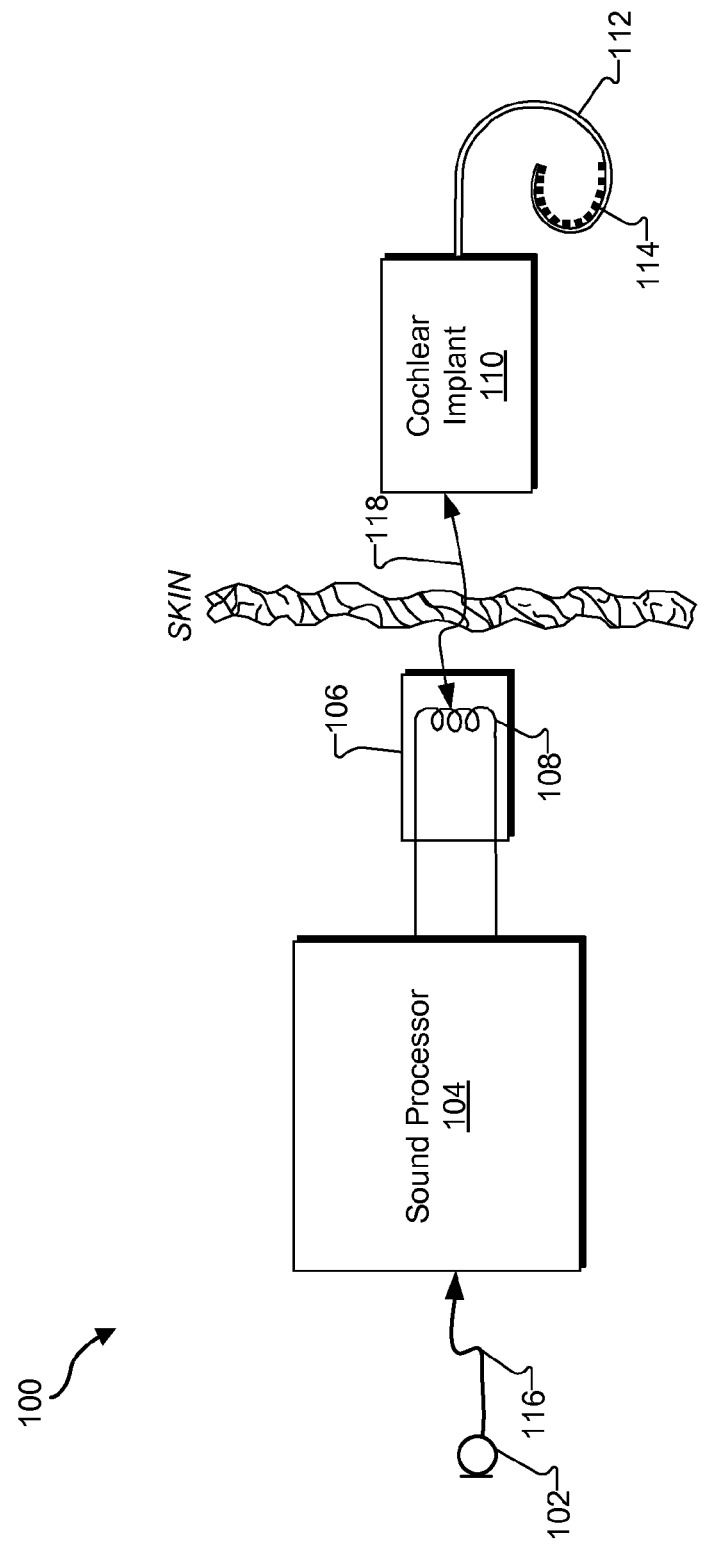
FIG. 1 illustrates an exemplary cochlear implant system according to principles described herein.

Methods and systems for managing cochlear implant fitting software are described herein. As described in more detail below, a cochlear implant fitting subsystem may be configured to maintain data representative of a cochlear implant fitting software package comprising a plurality of cochlear implant fitting features. The cochlear implant fitting subsystem may also be configured to maintain data representative of a plurality of independent licensing heuristics corresponding to the plurality of cochlear implant fitting features. For example, each independent licensing heuristic within the plurality of independent licensing heuristics may correspond to a different cochlear implant fitting feature within the plurality of cochlear implant fitting features. In addition, the cochlear implant fitting subsystem may be configured to selectively enable or disable each cochlear implant fitting feature in accordance with the corresponding independent licensing heuristic.

As used herein, the term "cochlear implant fitting feature" or "fitting feature" refers to any feature, option, tool, program, and/or function associated with the fitting of a cochlear implant system to a patient. For example, cochlear implant fitting features may include features, options, tools, programs, and/or functions associated with one or more sound processing operations, fitting operations, diagnostic operations, measurement operations, stimulation operations, neural response detection operations, control operations, and/or any other suitable operations of a cochlear implant fitting subsystem and/or cochlear implant system.

Numerous advantages may be associated with the methods and systems described herein. For example, a cochlear implant fitting software developer may create, test, release, and/or distribute a single cochlear implant fitting software package for use by a plurality of different cochlear implant fitting subsystems across a plurality of different geographic regions (e.g., countries, states, provinces, etc.) regardless of variances in regulatory restrictions and/or other limitations placed on the cochlear implant fitting software from one cochlear implant fitting subsystem and/or geographic region to the next. Thereafter, each cochlear implant fitting subsystem may selectively enable or disable each cochlear implant fitting feature of the software package in accordance with specific information associated with the fitting subsystem (e.g., a geographic location of the cochlear implant fitting subsystem, an association of the cochlear implant fitting subsystem with a clinical trial, a particular license purchased by a user of the cochlear implant fitting subsystem, etc.), and may thereby control access to one or more features of the software package on a feature-by-feature basis. As a result, the methods and systems described herein allow a cochlear implant fitting software developer to more easily and effectively manage the distribution and/or use of its cochlear implant fitting software.

To facilitate an understanding of the methods and systems described herein, an exemplary cochlear implant system 100 will be described in connection with FIG. 1. As shown in FIG. 1, cochlear implant system 100 may include a microphone 102, a sound processor 104, a headpiece 106 having a coil 108 disposed therein, a cochlear implant 110 (also referred to as an "implantable cochlear stimulator"), and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct cochlear implant 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling cochlear implant 110. Sound processor 104 may include or be implemented by a behind-the-ear ("BTE") unit, a portable speech processor ("PSP"), and/or any other sound-processing unit as may serve a particular implementation. Exemplary components of sound processor 104 will be described in more detail below.

Sound processor 104 may be configured to transcutaneously transmit, in accordance with a sound processing program associated with cochlear implant 110, one or more control parameters and/or one or more power signals to cochlear implant 110 with coil 108 by way of a communication link 118. These control parameters may be configured to specify one or more stimulation parameters, operating parameters, and/or any other parameter by which cochlear implant 110 is to operate as may serve a particular implementation. Exemplary control parameters include, but are not limited to, stimulation current levels, volume control parameters, program selection parameters, operational state parameters (e.g., parameters that turn a sound processor and/or a cochlear implant on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels ("T levels"), channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within cochlear implant 110. In this manner, control parameters and power signals may be wirelessly transmitted between sound processor 104 and cochlear implant 110 via communication link 118. It will be understood that data communication link 118 may include a bi-directional communication link and/or one or more dedicated uni-directional communication links. In some alternative embodiments, sound processor 104 and cochlear implant 110 may be directly connected with one or more wires or the like.

Cochlear implant 110 may be configured to generate electrical stimulation representative of an audio signal detected by microphone 102 in accordance with one or more stimulation parameters transmitted thereto by sound processor 104. Cochlear implant 110 may be further configured to apply the electrical stimulation to one or more stimulation sites within the cochlea via one or more electrodes 114 disposed along lead 112. In some examples, cochlear implant 110 may include a plurality of independent current sources, each associated with a channel defined by one or more of electrodes 114. In this manner, different stimulation current levels may be applied to different stimulation sites simultaneously by way of multiple electrodes 114. In such examples, cochlear implant system 100 may be referred to as a "multi-channel cochlear implant system."

To facilitate application of the electrical stimulation generated by cochlear implant 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
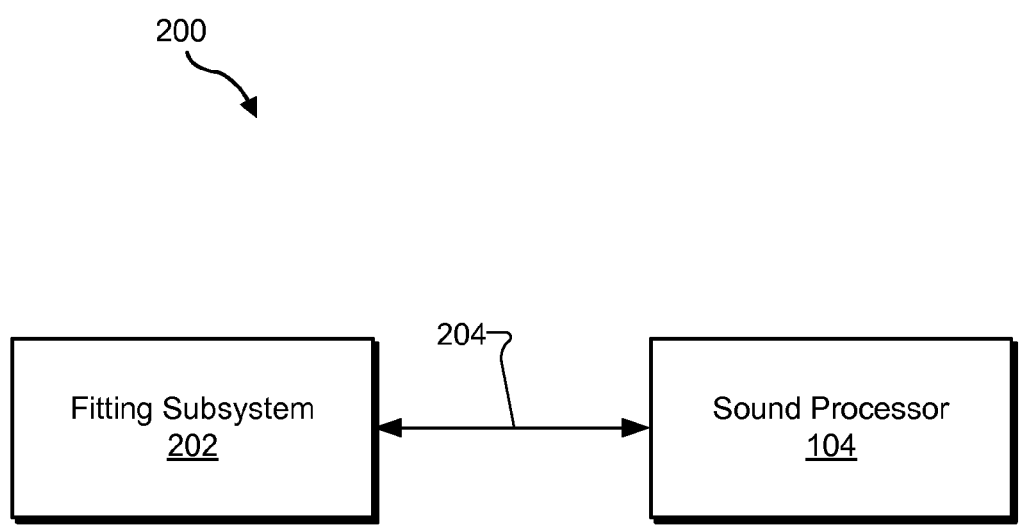
FIG. 2 illustrates an exemplary cochlear implant fitting system according to principles described herein.

FIG. 2 illustrates an exemplary cochlear implant fitting system 200 (or simply "fitting system 200") that may be used to fit sound processor 104 to a patient. As used herein, the terms "fitting a sound processor to a patient" and "fitting a cochlear implant to a patient" will be used interchangeably to refer to performing one or more fitting operations associated with sound processor 104, cochlear implant 110, and/or any other component of cochlear implant system 100. Such fitting operations may include, but are not limited to, adjusting one or more control parameters by which sound processor 104 and/or cochlear implant 110 operate, measuring one or more electrode impedances, performing one or more neural response detection operations, and/or performing one or more diagnostics procedures associated with cochlear implant system 100.

As shown in FIG. 2, fitting system 200 may include a cochlear implant fitting subsystem 202 (or simply "fitting subsystem 202") configured to be selectively and communicatively coupled to sound processor 104 of cochlear implant system 100 by way of a communication link 204. Fitting subsystem 202 and sound processor 104 may communicate using any suitable communication technologies, devices, networks, media, and protocols supportive of data communications.

Fitting subsystem 202 may be configured to perform one or more of the fitting operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation.

Figure 3:
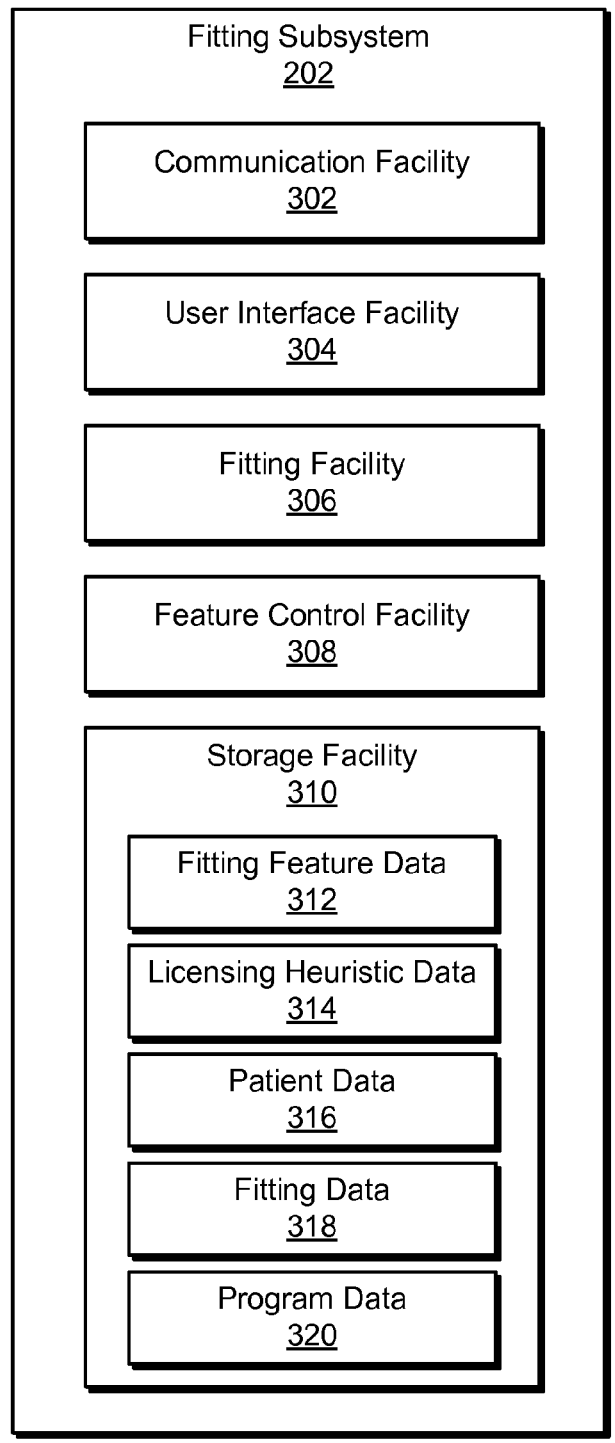
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a user interface facility 304, a fitting facility 306, a feature control facility 308, and a storage facility 310, which may be communicatively coupled to one another using any suitable communication technologies. Each of these facilities will now be described in more detail.

Communication facility 302 may be configured to facilitate communication between fitting subsystem 202 and sound processor 104. For example, communication facility 302 may be implemented by a CPI device, which may include any suitable combination of components configured to allow fitting subsystem 202 to interface and communicate with sound processor 104. Communication facility 302 may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104.

Communication facility 302 may be further configured to selectively communicate with cochlear implant 110 by way of sound processor 104 during a fitting process. For example, communication facility 302 may be configured to communicate with cochlear implant 110 when sound processor 104 is communicatively coupled (e.g., "locked") to cochlear implant 110.

Communication facility 302 may additionally or alternatively be configured to facilitate communication between fitting subsystem 302 and one or more other devices. For example, communication facility 302 may be configured to facilitate communication between fitting subsystem 302 and one or more computing devices (e.g., by way of the Internet and/or one or more other types of networks), reference implants, and/or any other computing device as may serve a particular implementation.

User interface facility 304 may be configured to provide one or more user interfaces configured to facilitate user interaction with fitting subsystem 202. For example, user interface facility 304 may provide a graphical user interface ("GUI") through which one or more cochlear implant fitting features described herein may be used by a user and through which user input may be received from the user. User interface facility 304 may be configured to provide the GUI to a display device (e.g., a computer monitor) for display. In some examples, the GUI may display information associated with a cochlear implant fitting software package (e.g., the GUI may display information associated with one or more cochlear implant fitting features included in the cochlear implant fitting software package). Additionally or alternatively, user interface facility 304 may be configured to facilitate the use and/or management of the cochlear implant fitting software package by way of the GUI, as will be explained in more detail below.

Fitting facility 306 may be configured to perform one or more of the fitting operations described herein. For example, fitting facility 306 may be configured to adjust one or more control parameters by which sound processor 104 and/or cochlear implant 110 operate, direct sound processor 104 to measure one or more electrode impedances, perform one or more neural response detection operations, and/or perform one or more diagnostics procedures associated with cochlear implant system 100.

In some examples, fitting facility 306 may be configured to perform one or more fitting operations in accordance with a cochlear implant fitting software package. For example, fitting facility 306 may be configured to perform the one or more fitting operations using one or more cochlear implant fitting features included within the cochlear implant fitting software package, as will be explained in more detail below.

In some examples, fitting facility 306 may be configured to initialize sound processor 104 prior to using sound processor 104 to fit cochlear implant 110 to a patient. Such initialization may include, but is not limited to, associating sound processor 104 with a particular patient (e.g., associating sound processor 104 with patient-specific fitting data), associating sound processor 104 with a particular cochlear implant 110, loading data onto sound processor 104, clearing data from sound processor 104, and/or otherwise preparing sound processor 104 for a fitting session in which sound processor 104 is to be fitted to a patient.

Feature control facility 308 may be configured to selectively enable or disable one or more cochlear implant fitting features included within a cochlear implant fitting software package. For example, an exemplary cochlear implant fitting software package may include a plurality of cochlear implant fitting features. The plurality of cochlear implant fitting features may correspond to a plurality of independent licensing heuristics. For example, each of the plurality of independent licensing heuristics may correspond to a different cochlear implant fitting feature. The independent licensing heuristics may be configured to govern the enablement or disablement of the corresponding cochlear implant fitting features. For example, each independent licensing heuristic may specify one or more licensing conditions to be satisfied in order for the corresponding cochlear implant fitting feature to be enabled.

The independent licensing heuristics may specify any suitable licensing conditions as may serve a particular implementation. For example, an exemplary licensing condition may be associated with a geographic region (e.g., the licensing condition may require that fitting subsystem 202 be physically located within a particular country), a clinical trial (e.g., the licensing condition may require that fitting subsystem 202 be associated with a particular clinical trial), a user (e.g., the licensing condition may require that fitting subsystem 202 be associated with a particular audiologist), a facility (e.g., the licensing condition may require that fitting subsystem 202 be associated with a particular clinic), a type of cochlear implant system (e.g., the licensing condition may require that fitting subsystem 202 be communicatively coupled to a particular type of sound processor or cochlear implant), a licensing key (e.g., the licensing condition may require the input of a unique alpha-numeric key), a time period (e.g., the licensing condition may specify a specific date on which a cochlear implant fitting feature will be enabled or disabled), and/or any other suitable information associated with fitting subsystem 202.

Feature control facility 308 may be configured to selectively enable or disable each cochlear implant fitting feature of a cochlear implant fitting software package in accordance with a corresponding independent licensing heuristic. For example, feature control facility 308 may be configured to detect whether one or more licensing conditions specified by a particular independent licensing heuristic have been satisfied, and enable or disable the corresponding cochlear implant fitting feature in response to the detection. To illustrate, if a particular independent licensing heuristic specifies a condition that fitting subsystem 202 be physically located within a particular geographic region (e.g., a particular country), feature control facility 308 may be configured to detect a physical location of fitting subsystem 202 and determine whether fitting subsystem 202 is physically located within the particular geographic region. If fitting subsystem 202 is physically located within the particular geographic region, feature control facility 308 may enable the corresponding cochlear implant fitting feature. If fitting subsystem 202 is physically located outside of the particular geographic, feature control facility 308 may disable the corresponding cochlear implant fitting feature. Feature control facility 308 may be configured to selectively enable or disable the cochlear implant fitting features in any other suitable manner.

Feature control facility 308 may be further configured to dynamically adapt to changing circumstances associated with each independent licensing heuristic. For example, feature control facility 308 may be configured to enable cochlear implant fitting features that were previously disabled and/or disable cochlear implant fitting features that were previously enabled, in accordance with changing circumstances affecting the corresponding independent licensing heuristics. To illustrate, in response to fitting subsystem 202 moving from a first geographic region to a second geographic region, feature control facility 308 may be configured to disable a first cochlear implant fitting feature associated with the first geographic region and enable a second cochlear implant fitting feature associated with the second geographic region in accordance with corresponding independent licensing heuristics. Feature control facility 308 may be configured to dynamically enable or disable cochlear implant fitting features in any other suitable manner.

Additionally or alternatively, feature control facility 308 may be configured to override one or more independent licensing heuristics to use one or more corresponding cochlear implant fitting features. To illustrate, feature control facility 308 may be configured to detect what cochlear implant fitting features have been previously used to fit sound processor 104 and/or cochlear implant 110. For example, feature control facility 308 may be configured to receive data from sound processor 104 identifying one or more cochlear implant fitting features previously used by an audiologist to fit sound processor 104 and/or cochlear implant 110 to a cochlear implant patient. In some examples, the one or more cochlear implant fitting features may be disabled on fitting subsystem 202 in accordance with one or more corresponding independent licensing heuristics. In response to detecting that the one or more disabled cochlear implant fitting features were previously used to fit sound processor 104 and/or cochlear implant 110 to the patient, feature control facility 308 may be configured to override the one or more corresponding independent licensing heuristics. After overriding the one or more corresponding independent licensing heuristics, fitting subsystem 202 may be configured to perform one or more fitting operations in accordance with the one or more disabled cochlear implant fitting features. This may allow an audiologist to use fitting subsystem 202 to perform the one or more fitting operations for the patient, despite a failure to satisfy the licensing conditions specified by the one or more corresponding independent licensing heuristics. In other words, fitting subsystem 202 may be configured to make an exception to conditions specified by an independent licensing heuristic in order to allow the patient to continue to have access to one or more fitting features that were used previously to fit sound processor 104 and/or cochlear implant 110 to the patient. In response to a communicative decoupling of fitting subsystem 202 from sound processor 104 (e.g., after the one or more fitting operations are performed), fitting subsystem 202 may restore the overridden independent licensing heuristics.

In some examples, feature control facility 308 may be further configured to disable an enabled cochlear implant fitting feature after the cochlear implant fitting feature expires. For example, a particular cochlear implant fitting feature may be configured to expire after a predetermined period of time, after a predetermined number of uses, or on a predetermined date. To illustrate, the particular cochlear implant fitting feature may be associated with a clinical trial that ends on a particular date or after a predetermined number of uses. Accordingly, feature control facility 308 may be configured to track the dates of use and/or number of uses of the particular cochlear implant fitting feature. Once the clinical trial ends, feature control facility 308 may be configured to disable the particular cochlear implant fitting feature.

Feature control facility 308 may be configured to perform any other suitable operations associated with the management of a cochlear implant fitting software package including a plurality of cochlear implant fitting features.

Storage facility 310 may be configured to maintain fitting feature data 312 representative of one or more cochlear implant fitting features, licensing heuristic data 314 representative of one or more independent licensing heuristics, patient data 316 representative of data descriptive of or otherwise associated with one or more cochlear implant patients, control parameter data 318 representative of one or more control parameters, and program data 320 representative of one or more sound processing programs, any or all of which may be maintained within one or more data sets. Storage facility 310 may be configured to maintain additional or alternative data as may serve a particular implementation.

Figure 4:
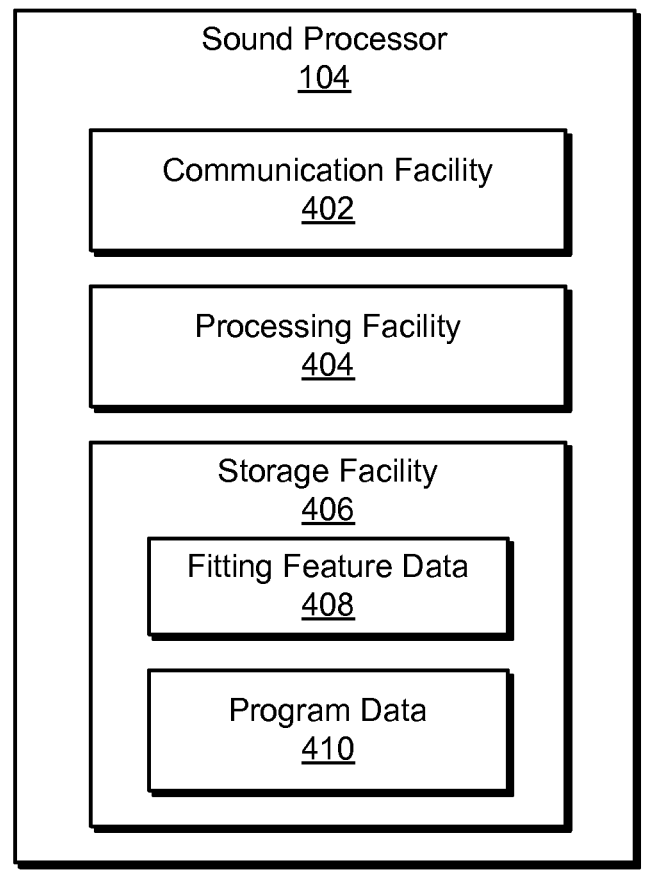
FIG. 4 illustrates exemplary components of an exemplary sound processor according to principles described herein.

FIG. 4 illustrates exemplary components of sound processor 104. As shown in FIG. 4, sound processor 104 may include a communication facility 402, a processing facility 404, and a storage facility 406, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and cochlear implant 110. For example, communication facility 402 may include transceiver components configured to wirelessly transmit data (e.g., control parameters and/or power signals) to cochlear implant 110 and/or wirelessly receive data from cochlear implant 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of cochlear implant 110 (e.g., one or more stimulation parameters defining the electrical stimulation to be generated and applied by cochlear implant 110). In some examples, processing facility 404 may be configured to operate in accordance with one or more sound processing programs provided by fitting subsystem 202 and/or otherwise stored within storage facility 406.

Storage facility 406 may be configured to maintain fitting feature data 408 representative of one or more cochlear implant fitting features used to fit sound processor 104 to a patient and program data 410 representative of one or more sound processing programs. Storage facility 406 may be configured to maintain additional or alternative data as may serve a particular implementation.

Figure 5:
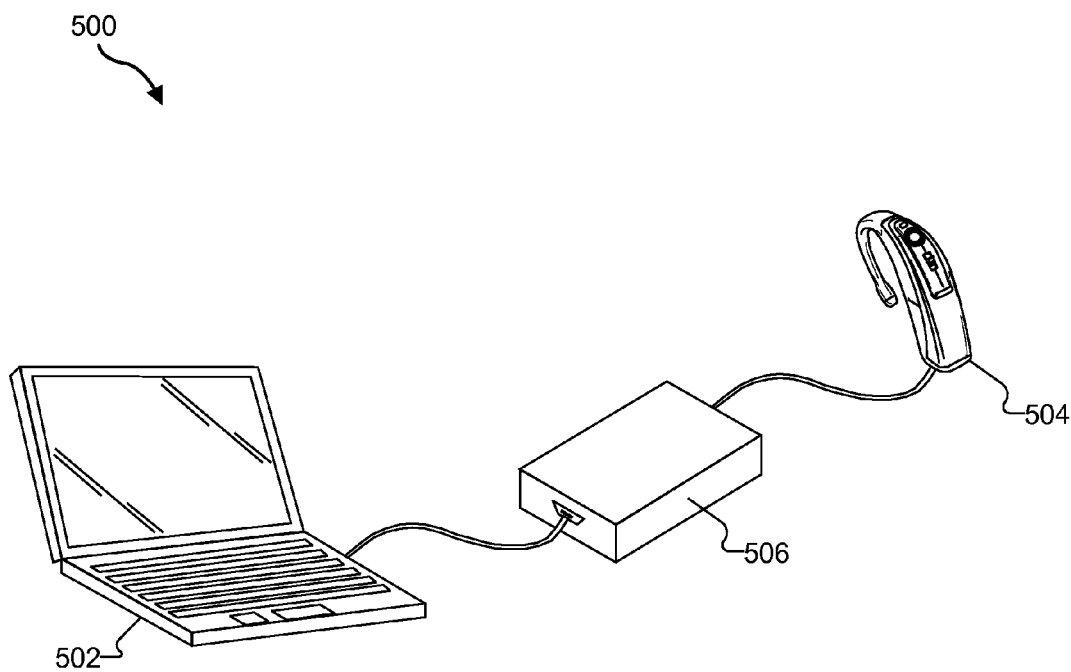
FIG. 5 illustrates an exemplary implementation of the cochlear implant fitting system of FIG. 2 according to principles described herein.

FIG. 5 illustrates an exemplary implementation 500 of fitting system 200. In implementation 500, a fitting station 502 may be selectively and communicatively coupled to a BTE unit 504 by way of a CPI device 506. BTE unit 504 is merely exemplary of the many different types of sound processors that may be used in accordance with the systems and methods described herein. Fitting station 502 may be selectively and communicatively coupled to any other type of sound processor as may serve a particular implementation.

Fitting station 502 may include any suitable computing device and/or combination of computing devices and may be configured to perform one or more of the fitting operations described herein. For example, fitting station 502 may display one or more GUIs configured to facilitate selection of one or more measurements to perform using BTE unit 504, selection of one or more sound processing programs by which BTE unit 504 operates, adjustment of one or more control parameters by which BTE unit 504 operates, and/or any other fitting operation as may serve a particular implementation. Fitting station 502 may be utilized by an audiologist, a clinician, and/or any other user to fit one or more cochlear implants to a patient using BTE unit 504.

BTE unit 504 may be configured to selectively and communicatively couple to a cochlear implant (e.g., cochlear implant 110). In this manner, BTE unit 504 may be configured to facilitate the fitting of the cochlear implant by fitting station 502.

CPI device 506 may be configured to facilitate communication between fitting station 502 and BTE unit 504. In some examples, CPI device 506 may be selectively and communicatively coupled to fitting station 502 and/or BTE unit 504 by way of one or more ports included within fitting station 502 and BTE unit 504.

Figure 6:
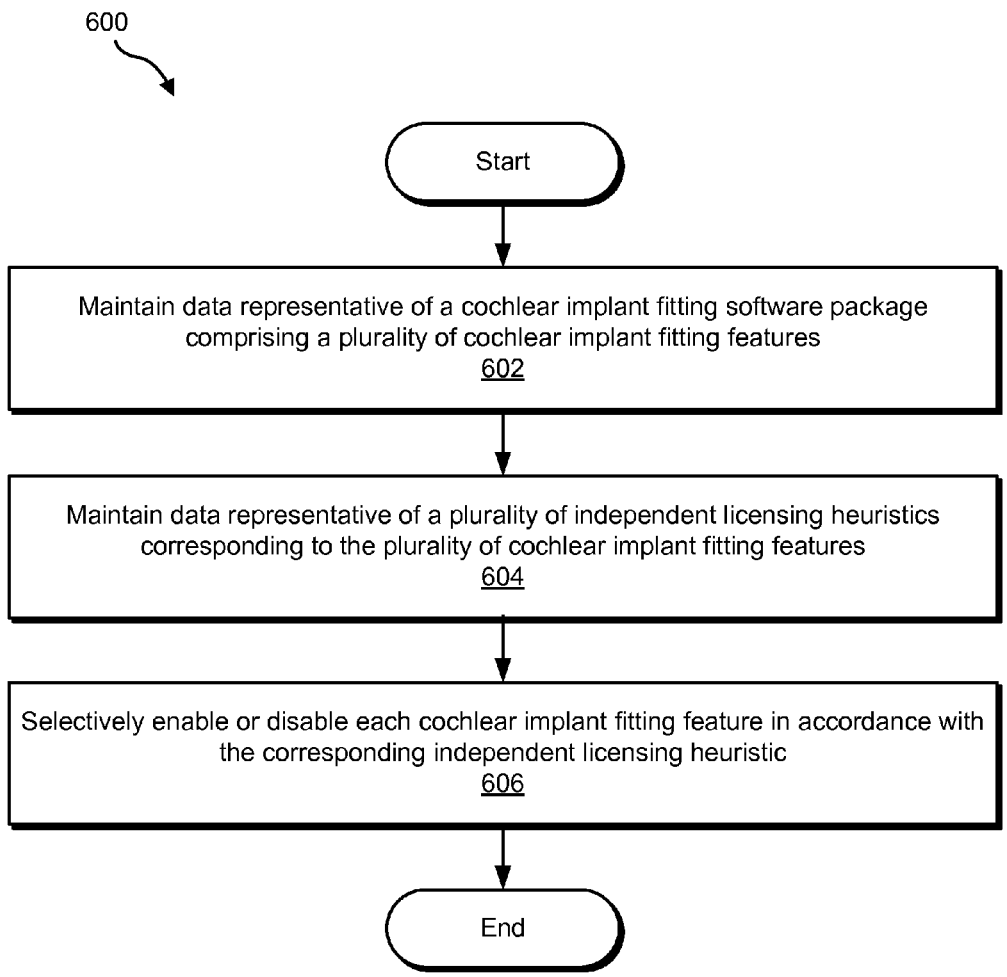
FIG. 6 illustrates an exemplary method of managing cochlear implant fitting software according to principles described herein.

FIG. 6 illustrates an exemplary method 600 of managing cochlear implant fitting software. While FIG. 6 illustrates exemplary steps according to one embodiment, other embodiments may omit, add to, reorder, and/or modify any of the steps shown in FIG. 6. One or more of the steps shown in FIG. 6 may be performed by any component or combination of components of fitting subsystem 202 and/or fitting station 502.

In step 602, a cochlear implant fitting subsystem maintains data representative of a cochlear implant fitting software package comprising a plurality of cochlear implant fitting features. For example, storage facility 310 may be configured to maintain the data representative of the cochlear implant fitting software package in any suitable manner, such as described herein.

Figure 7:
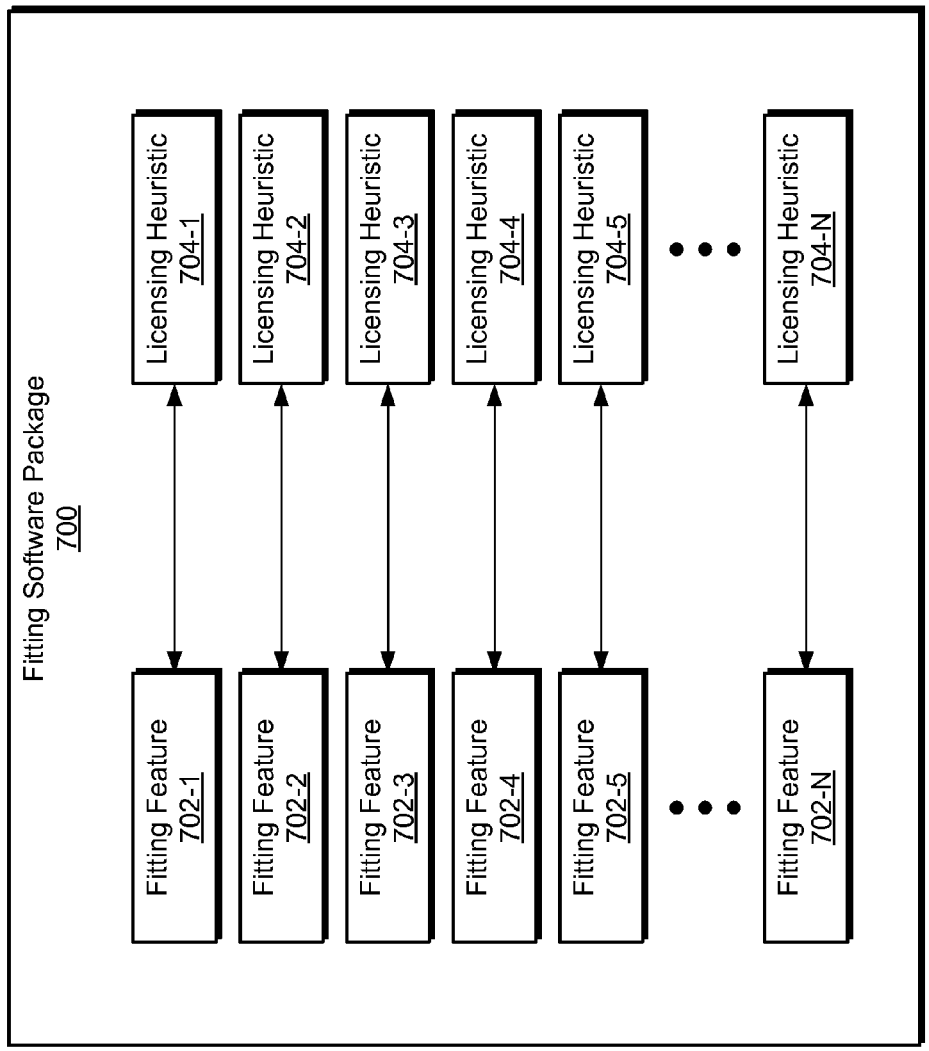
FIG. 7 illustrates an exemplary cochlear implant fitting software package according to principles described herein.

FIG. 7 illustrates a block diagram of an exemplary cochlear implant fitting software package 700 (or simply "fitting software package 700") that may be maintained by fitting subsystem 202. As shown, fitting software package 700 may be configured to include a plurality of cochlear implant fitting features 702-1 through 702-N (collectively referred to herein as "fitting features 702"). Fitting features 702 may include any suitable cochlear implant fitting features, such as those described herein. In addition, although FIG. 7 illustrates a certain number of fitting features 702, in further embodiments fitting software package 700 may include any number of fitting features 702 as may serve a particular implementation.

Returning to FIG. 6, in step 604, the cochlear implant fitting subsystem maintains data representative of a plurality of independent licensing heuristics corresponding to the plurality of cochlear implant fitting features. In some examples, each independent licensing heuristic within the plurality of independent licensing heuristics may correspond to a different cochlear implant fitting feature within the plurality of cochlear implant fitting features. Storage facility 310 may be configured to maintain the data representative of the plurality of independent licensing heuristics in any suitable manner, such as described herein.

As shown in FIG. 7, fitting software package 700 may also include a plurality of independent licensing heuristics 704-1 through 704-N (collectively referred to herein as "licensing heuristics 704"). As shown, each of licensing heuristics 704 may correspond to a different fitting feature of fitting features 702 (e.g., licensing heuristic 704-1 may correspond to fitting feature 702-1, licensing heuristic 704-2 may correspond to fitting feature 702-2, and so on). Licensing heuristics 704 may include any suitable independent licensing heuristics, such as those described herein. In addition, each of licensing heuristics 704 may specify any suitable licensing condition(s), such as those described herein.

Returning to FIG. 6, in step 606, the cochlear implant fitting subsystem selectively enables or disables each cochlear implant fitting feature in accordance with the corresponding independent licensing heuristic. For example, feature control facility 308 may be configured to selectively enable or disable each cochlear implant fitting feature in any suitable manner, such as described herein.

To illustrate, and returning to FIG. 7, fitting subsystem 202 may be configured to selectively enable or disable each of fitting features 702 in accordance with licensing heuristics 704. For example, fitting subsystem 202 may be configured to detect if one or more licensing conditions specified by licensing heuristic 704-1 are satisfied. In response to a detection by fitting subsystem 202 that the one or more licensing conditions specified by licensing heuristic 704-1 are satisfied, fitting subsystem 202 may enable fitting feature 702-1. In response to a detection that the one or more licensing conditions specified by licensing heuristic 704-1 are not satisfied, fitting subsystem 202 may disable fitting feature 702-1. In this or a similar manner, fitting feature 702-1 may be individually enabled or disabled independently of other fitting features 702-2 through 702-N. The process may be performed for each of fitting features 702-2 through 702-N in accordance with licensing heuristics 704-2 through 704-N. In some examples, fitting subsystem 202 may continue to selectively and independently enable or disable fitting features 702 on an ongoing basis, and dynamically adapt in response to any changed circumstances affecting licensing heuristics 704.

Figure 8:
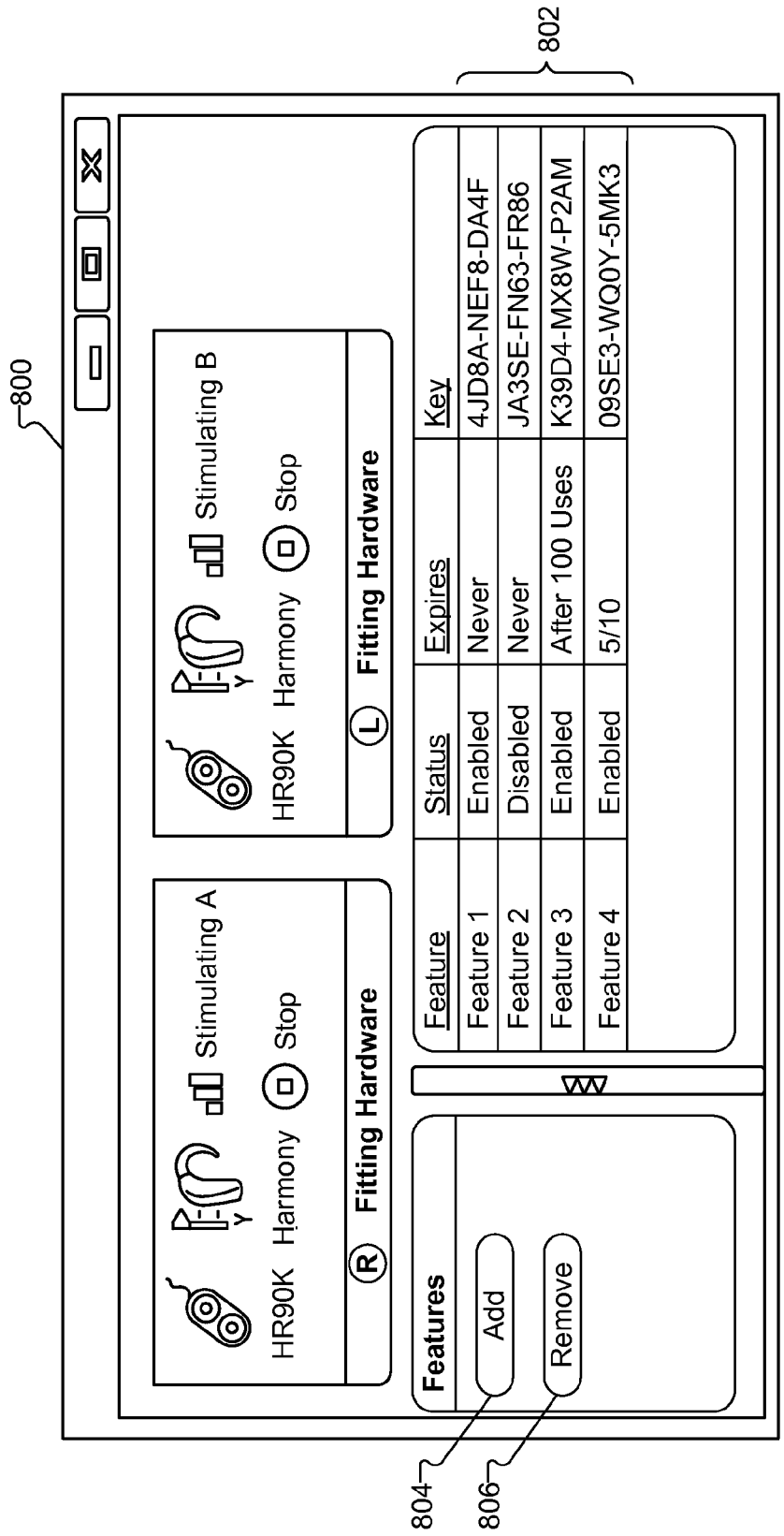
FIG. 8 shows an exemplary graphical user interface ("GUI") that may be presented for display according to principles described herein.

As mentioned above, fitting subsystem 202 may be configured to provide a GUI for display to a user. FIG. 8 includes an exemplary GUI 800 that may be provided by fitting subsystem 202 for display to a user. As shown, GUI 800 may display information associated with fitting components (e.g., one or more sound processors and/or cochlear implants) communicatively coupled to fitting subsystem 202. In addition, GUI 800 may display a listing 802 of cochlear implant fitting features. For example, listing 802 may include one or more cochlear implant features from a cochlear implant fitting software package maintained by fitting subsystem 202. For each cochlear implant fitting feature included in listing 802, listing 802 may display an associated status (e.g., information indicating whether the cochlear implant fitting feature is enabled or disabled), an associated expiration (e.g., information indicating whether the cochlear implant will expire and, if so, the conditions of the expiration), and an associated key (e.g., a unique alpha-numeric key associated with the cochlear implant fitting feature).

In some examples, a user may use GUI 800 to add cochlear implant fitting features to listing 802. For example, GUI 800 may include an option 804 configured to facilitate the addition of a cochlear implant fitting feature to listing 802. To illustrate, in response to a selection of option 804, GUI 800 may prompt the user for information identifying the cochlear implant fitting feature the user wishes to add to listing 802 (e.g., GUI 800 may prompt the user for entry of a unique alpha-numeric key associated with the cochlear implant fitting feature the user wishes to add to listing 802). Once the cochlear implant fitting feature is added to listing 802, GUI 800 may display a status, an expiration, and a key associated with the added cochlear implant fitting feature. In some examples, adding a cochlear implant fitting feature to listing 802 may facilitate the enablement of the added cochlear implant fitting feature. For example, in response to detecting a user input of a unique alpha-numeric key by way of GUI 800 and/or the satisfaction of one or more corresponding licensing conditions, fitting subsystem 202 may be configured to enable the added cochlear implant fitting feature and make it available for use by fitting subsystem 202.

Additionally or alternatively, GUI 800 may include an option 806 configured to facilitate a removal of one or more cochlear implant fitting features from listing 802. For example, a user may select a cochlear implant fitting feature from listing 802 and then select option 806 to remove the selected cochlear implant fitting feature from listing 802.

Figure 9:
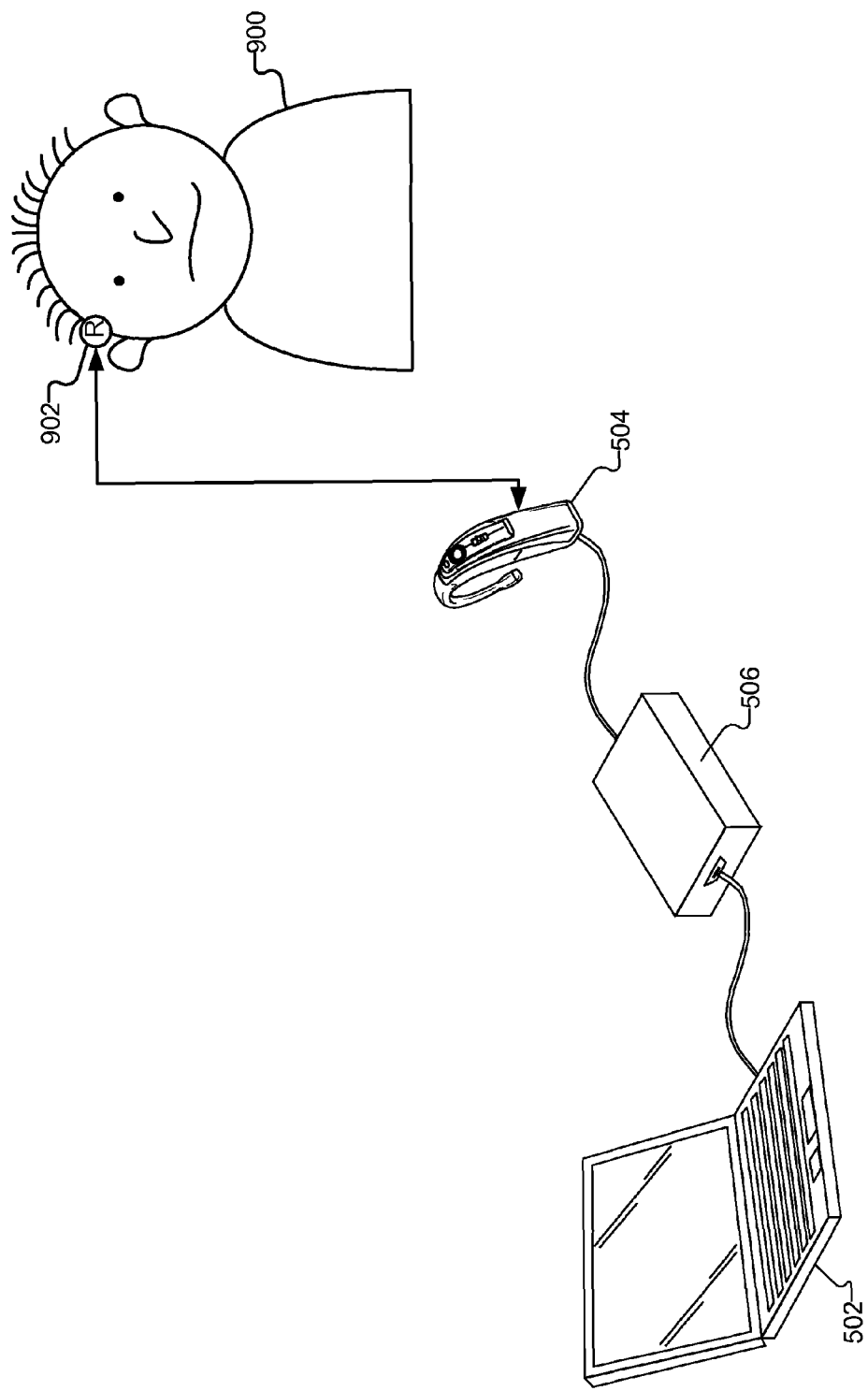
FIG. 9 illustrates an exemplary cochlear implant patient being fitted by the fitting components of FIG. 5 according to principles described herein.

Fitting subsystem 202 may be additionally or alternatively configured to selectively override one or more independent licensing heuristics in accordance with the fitting of a cochlear implant patient. To illustrate, FIG. 9 shows an exemplary cochlear implant patient 900 being fitted by the fitting components described in connection with FIG. 5. As shown in FIG. 9, patient 900 may have a cochlear implant 902 associated with the patient's right ear. Cochlear implant 902 may be implanted in patient 900 using any suitable technique as may serve a particular implementation.

In some examples, BTE unit 504 may have been previously fitted to patient 900 using one or more cochlear implant fitting features that are disabled on fitting station 502 (e.g., prior to being communicatively coupled to fitting station 502, BTE unit 504 may have been fitted to patient 900 using another fitting station on which the one or more cochlear implant fitting features were enabled). Fitting station 502 may be configured to detect that BTE unit 504 was previously fitted to patient 900 using one or more cochlear implant fitting features that are disabled on fitting station 502. The detection may be performed in any suitable manner as may serve a particular implementation. For example, fitting station 502 may detect and process fitting feature data (e.g., fitting feature data 408) stored by BTE unit 504 and representative of the one or more cochlear implant fitting features. Additionally or alternatively, fitting feature data associated with the patient may be imported into fitting station 502 using an export file or the like.

The one or more cochlear implant fitting features may be disabled on fitting station 502 in accordance with one or more corresponding independent licensing heuristics. In response to the detection that BTE unit 504 was previously fitted to patient 900 using the one or more disabled cochlear implant fitting features, fitting station 502 may override the one or more corresponding independent licensing heuristics and perform one or more fitting operations in accordance with the one or more disabled cochlear implant fitting features. As a result, fitting station 502 may allow an audiologist to fit BTE unit 504 to patient using the same cochlear implant fitting features that were previously used to fit BTE unit 504 to patient 900, despite the cochlear implant fitting features being otherwise disabled on fitting station 502.

Figure 10:
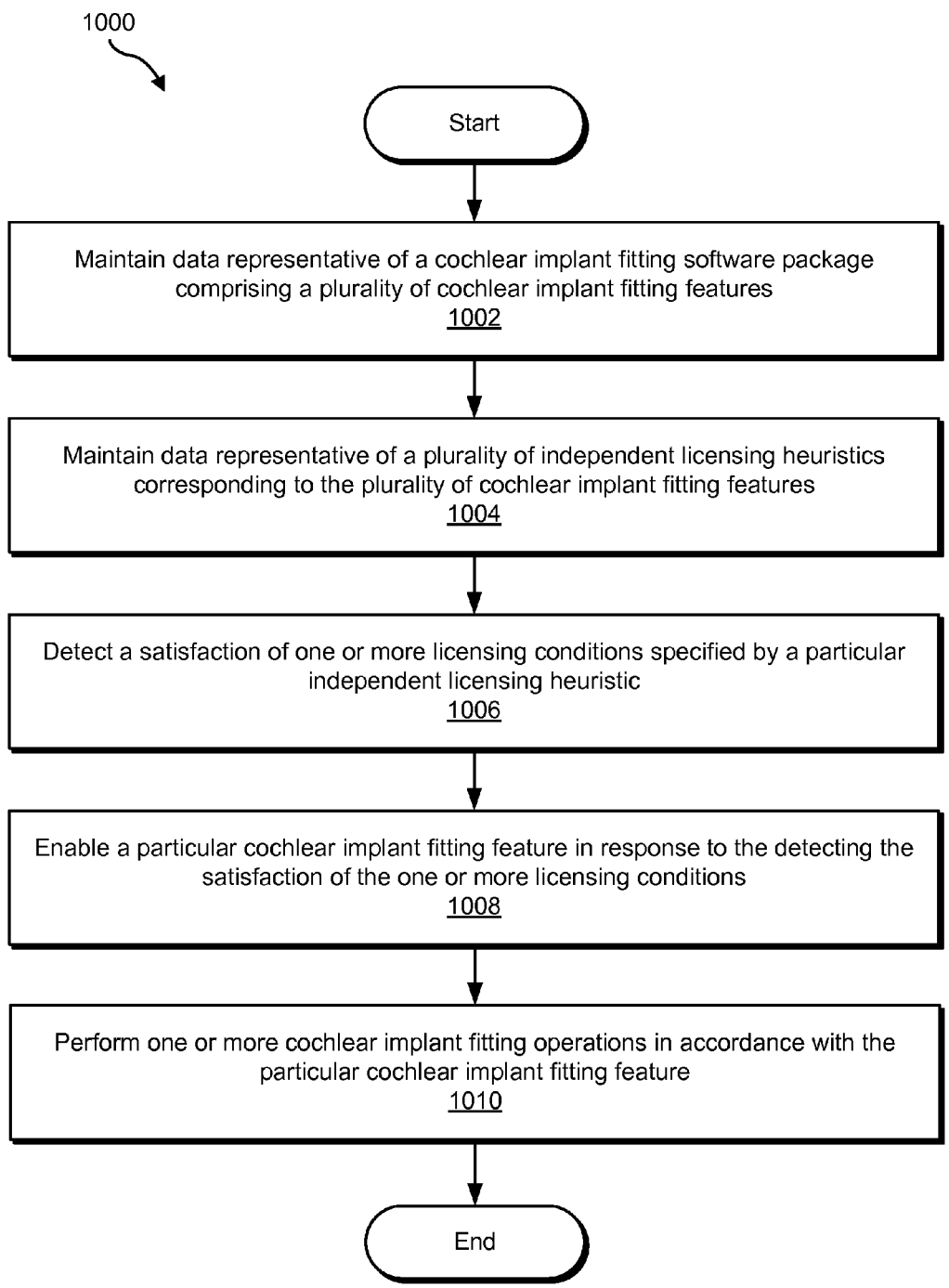
FIG. 10 illustrates another exemplary method of managing cochlear implant fitting software according to principles described herein.

FIG. 10 illustrates another exemplary method 1000 of managing cochlear implant fitting software. While FIG. 10 illustrates exemplary steps according to one embodiment, other embodiments may omit, add to, reorder, and/or modify any of the steps shown in FIG. 10. One or more of the steps shown in FIG. 10 may be performed by any component or combination of components of fitting subsystem 202 and/or fitting station 502.

In step 1002, a cochlear implant fitting subsystem maintains data representative of a cochlear implant fitting software package comprising a plurality of cochlear implant fitting features. The cochlear implant fitting subsystem may be configured to maintain the data representative of the cochlear implant fitting software package in any suitable manner, such as described herein.

In step 1004, the cochlear implant fitting subsystem maintains data representative of a plurality of independent licensing heuristics corresponding to the plurality of cochlear implant fitting features. The cochlear implant fitting subsystem may be configured to maintain the data representative of the plurality of independent licensing heuristics in any suitable manner, such as described herein.

In step 1006, the cochlear implant fitting subsystem detects a satisfaction of one or more licensing conditions specified by a particular independent licensing heuristic. The particular independent licensing heuristic may be one of the plurality of independent licensing heuristics. Cochlear implant fitting subsystem may be configured to detect the satisfaction of the one or more licensing conditions specified by the particular independent licensing heuristic in any suitable manner, such as described herein.

In step 1008, the cochlear implant fitting subsystem enables a particular cochlear implant fitting feature in response to the detecting the satisfaction of the one or more licensing conditions. The particular cochlear implant fitting feature may correspond to the particular independent licensing heuristic. The cochlear implant fitting subsystem may be configured to enable the particular cochlear implant fitting feature in any suitable manner, such as described herein.

In step 1010, the cochlear implant fitting subsystem performs one or more cochlear implant fitting operations in accordance with the particular cochlear implant fitting feature. The cochlear implant fitting subsystem may be configured to perform the one or more cochlear implant fitting operations in any suitable manner, such as described herein.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 11:
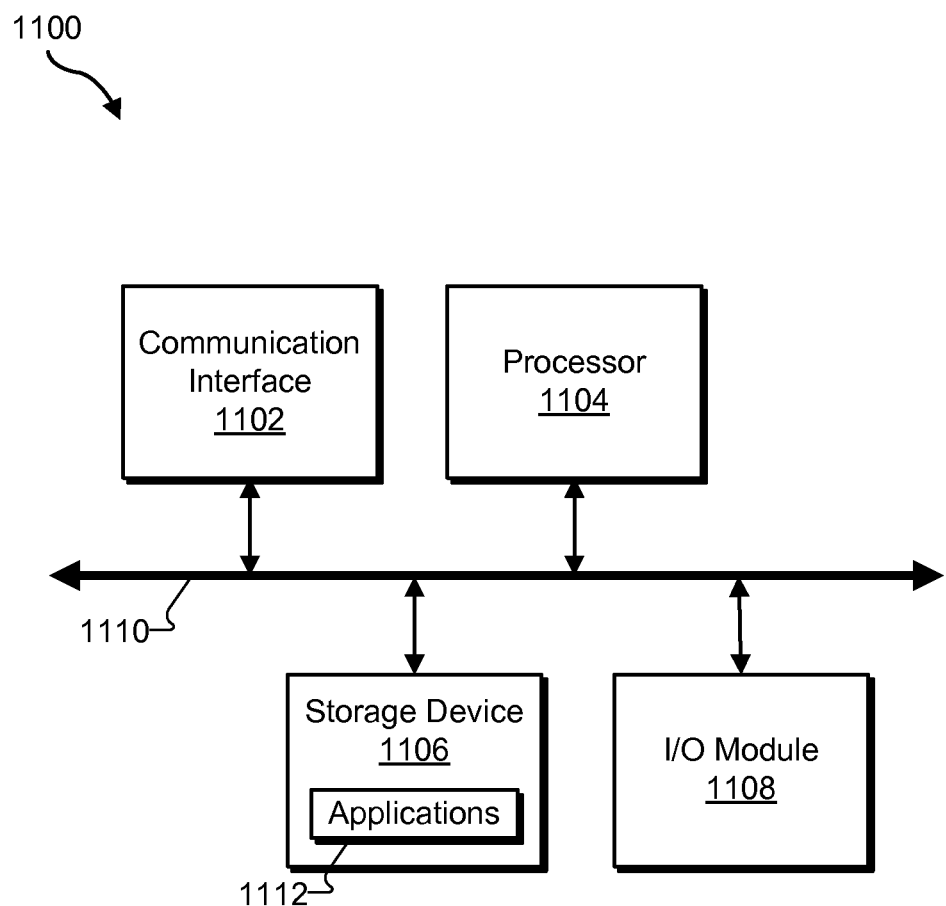
FIG. 11 illustrates an exemplary computing device according to principles described herein.

FIG. 11 illustrates an exemplary computing device 1100 that may be configured to perform one or more of the processes described herein. As shown in FIG. 11, computing device 1100 may include a communication interface 1102, a processor 1104, a storage device 1106, and an input/output ("I/O") module 1108 communicatively connected via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, and any other suitable interface. Communication interface 1102 may additionally or alternatively provide such a connection through, for example, a local area network (such as an Ethernet network), a personal area network, a telephone or cable network, a satellite data connection, a dedicated URL, or any other suitable connection. Communication interface 1102 may be configured to interface with any suitable communication media, protocols, and formats, including any of those mentioned above.

Processor 1104 generally represents any type or form of processing unit capable of processing data or interpreting, executing, and/or directing execution of one or more of the instructions, processes, and/or operations described herein. Processor 1104 may direct execution of operations in accordance with one or more applications 1112 or other computer-executable instructions such as may be stored in storage device 1106 or another non-transitory computer-readable medium.

Storage device 1106 may include one or more data storage media, devices, or configurations and may employ any type, form, and combination of data storage media and/or device. For example, storage device 1106 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1106. For example, data representative of one or more executable applications 1112 (which may include, but are not limited to, one or more of the software applications described herein) configured to direct processor 1104 to perform any of the operations described herein may be stored within storage device 1106. In some examples, data may be arranged in one or more databases residing within storage device 1106.

I/O module 1108 may be configured to receive user input and provide user output and may include any hardware, firmware, software, or combination thereof supportive of input and output capabilities. For example, I/O module 1108 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1108 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1100. For example, one or more applications 1112 residing within storage device 1106 may be configured to direct processor 1104 to perform one or more processes or functions associated with communication facility 302, user interface facility 304, fitting facility 306, feature control facility 308, communication facility 402, and/or processing facility 404. Likewise, storage facility 310 and/or storage facility 406 may be implemented by or within storage device 1106.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
   maintaining, by a cochlear implant fitting subsystem, data representative of a licensing heuristic;
   maintaining, by the cochlear implant fitting subsystem, data representative of a cochlear implant fitting software package comprising a cochlear implant fitting feature that is disabled in accordance with the licensing heuristic;
   detecting, by the cochlear implant fitting subsystem, that the cochlear implant fitting subsystem is communicatively coupled to a sound processor previously fitted using the disabled cochlear implant fitting feature;
   overriding, by the cochlear implant fitting subsystem in response to the detecting of the communicative coupling, the licensing heuristic corresponding to the disabled cochlear implant fitting feature; and
   performing, by the cochlear implant fitting subsystem, one or more cochlear implant fitting operations in accordance with the one or more disabled cochlear implant fitting feature.

2. The method of claim 1, wherein the cochlear implant fitting software package further comprises an additional cochlear implant fitting feature, and wherein the method further comprises:
   maintaining, by the cochlear implant fitting subsystem, data representative of an additional licensing heuristic corresponding to the additional cochlear implant fitting feature and specifying one or more licensing conditions;
   detecting, by the cochlear implant fitting subsystem, whether the one or more licensing conditions are satisfied;
   selectively enabling, by the cochlear implant fitting subsystem, the additional cochlear implant fitting feature in accordance with the additional licensing heuristic if the one or more licensing conditions are satisfied; and
   selectively disabling, by the cochlear implant fitting subsystem, the additional cochlear implant fitting feature in accordance with the additional licensing heuristic if the one or more licensing conditions are not satisfied.

3. The method of claim 2, wherein:
   the one or more licensing conditions require that the cochlear implant fitting subsystem be physically located within a predetermined geographic region; and
   the detecting comprises detecting whether the cochlear implant fitting subsystem is physically located within the predetermined geographic region.

4. The method of claim 2, wherein:
   the one or more licensing conditions require that the cochlear implant fitting subsystem be associated with a particular clinical trial; and
   the detecting comprises detecting whether the cochlear implant fitting subsystem is associated with the particular clinical trial.

5. The method of claim 2, wherein:
   the one or more licensing conditions require entry by a user of a unique alpha-numeric key; and
   the detecting comprises detecting whether the user has input of the unique alpha-numeric key.

6. The method of claim 2, wherein the one or more licensing conditions are satisfied, and wherein the method further comprises disabling, by the cochlear implant fitting subsystem, the additional cochlear implant fitting feature a predetermined period of time subsequent to the enabling of the additional cochlear implant fitting feature.

7. The method of claim 2, wherein the one or more licensing conditions are satisfied, and wherein the method further comprises disabling, by the cochlear implant fitting subsystem, the additional cochlear implant fitting feature on a predetermined date subsequent to the enabling of the additional cochlear implant fitting feature.

8. The method of claim 2, wherein the one or more licensing conditions are satisfied, and wherein the method further comprising performing, by the cochlear implant fitting subsystem, one or more cochlear implant fitting operations in accordance with the additional cochlear implant fitting feature after the enabling of the additional cochlear implant fitting feature.

9. The method of claim 1, further comprising:
detecting, by the cochlear implant fitting subsystem, a communicative decoupling of the cochlear implant fitting subsystem from the sound processor; and
restoring, by the cochlear implant fitting subsystem in response to the detecting the communicative decoupling, the licensing heuristic.

10. The method of claim 2, wherein the selectively enabling or the disabling of the additional cochlear implant fitting feature comprises dynamically enabling or disabling the additional cochlear implant fitting feature in accordance with a change associated with the additional licensing heuristic.

11. The method of claim 2, embodied as computer-executable instructions on at least one non-transitory computer-readable medium.

12. The method of claim 2, wherein the one or more licensing conditions are satisfied, and wherein the method further comprises disabling, by the cochlear implant fitting subsystem, the additional cochlear implant fitting feature in response a predetermined number of uses of the additional cochlear implant fitting feature subsequent to the enabling of the additional cochlear implant fitting feature.

13. The method of claim 2, wherein the cochlear implant fitting software package further comprises a second additional cochlear implant feature, and wherein the method further comprises:
maintaining, by the cochlear implant fitting subsystem, data representative of a second additional licensing heuristic corresponding to the second additional cochlear implant fitting feature and specifying one or more additional licensing conditions; and
detecting, by the cochlear implant fitting subsystem, whether the one or more additional licensing conditions are satisfied;
selectively enabling, by the cochlear implant fitting subsystem, the second additional cochlear implant fitting feature in accordance with the second additional licensing heuristic if the one or more licensing additional conditions are satisfied; and
selectively disabling, by the cochlear implant fitting subsystem, the second additional cochlear implant fitting feature in accordance with the second additional licensing heuristic if the one or more additional licensing conditions are not satisfied.

\* \* \* \* \*